United States Patent [19]

Weintraub et al.

[11] Patent Number: 4,635,638
[45] Date of Patent: Jan. 13, 1987

[54] POWER-DRIVEN GRIPPING TOOL PARTICULARLY USEFUL AS A SUTURING DEVICE

[75] Inventors: David Weintraub, Kibbutz Dvir; Yaakov Zamir, Kfar Saba, both of Israel

[73] Assignee: Galil Advanced Technologies Ltd., Ramat Gan, Israel

[21] Appl. No.: 696,103

[22] Filed: Jan. 29, 1985

[30] Foreign Application Priority Data

Feb. 7, 1984 [IL] Israel .................................... 70893

[51] Int. Cl.⁴ ...................... A61B 17/06; A61B 17/04; B23Q 3/08; B25B 1/02
[52] U.S. Cl. ................................... 128/340; 128/321; 269/140; 269/25

[58] Field of Search ............. 128/340, 334 R, 92 EC, 128/321, 322; 269/140, 25, 91, 43, 254 CS; 81/301, 303, 305, 304, 306, 307; 173/168, 169, 170

[56] References Cited

U.S. PATENT DOCUMENTS

4,109,658 8/1978 Hughes .............................. 128/340

Primary Examiner—Richard C. Pinkham
Assistant Examiner—Garg Jackson
Attorney, Agent, or Firm—Benjamin J. Barish

[57] ABSTRACT

A power-driven gripping tool particularly useful as a suturing device comprises a pair of needle holders each movable to an extended or retracted position and each including a pair of gripper members movable to a gripping position or to a releasing position. The handle further includes a power drive for driving the pair of needle holders and the pair of gripper members of each needle holder; and control means operable by the surgeon for selectively controlling the power drive.

20 Claims, 12 Drawing Figures

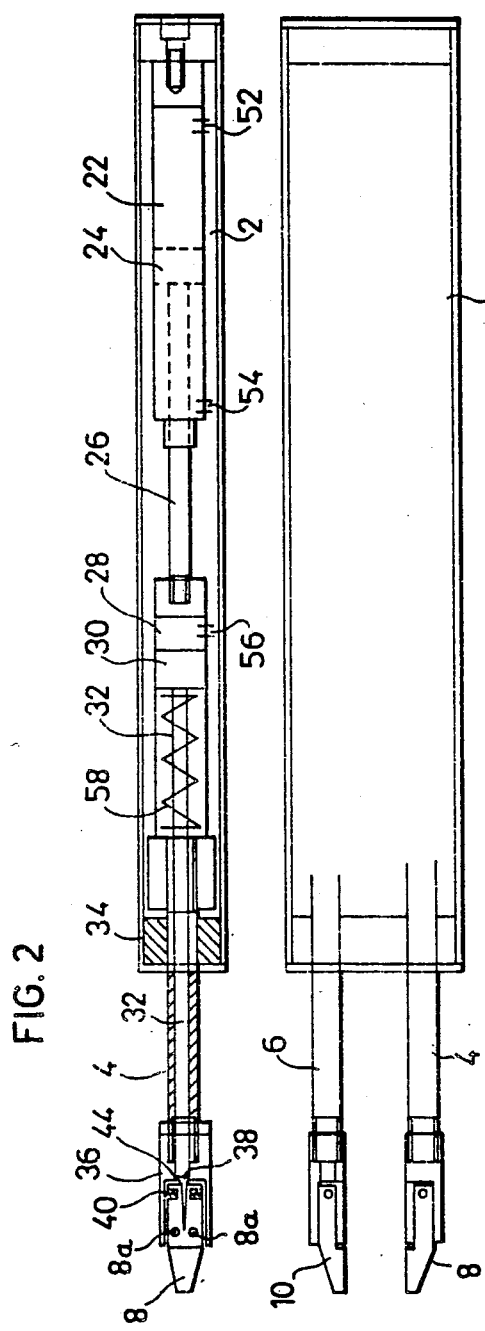
FIG. 2
FIG. 3
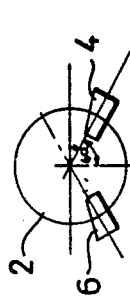
FIG. 4
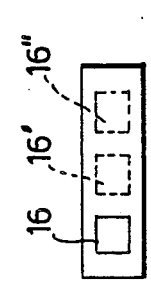
FIG. 7
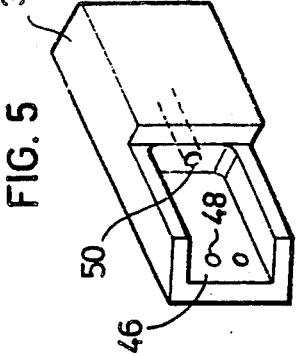
FIG. 6
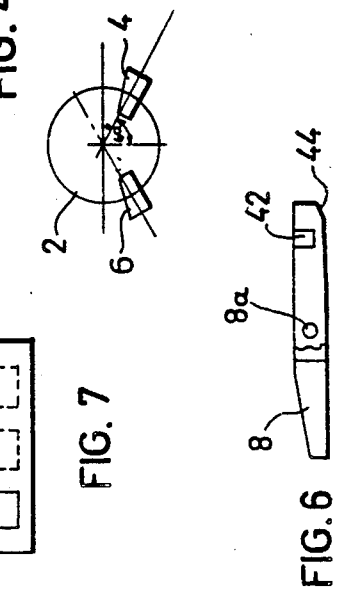
FIG. 5

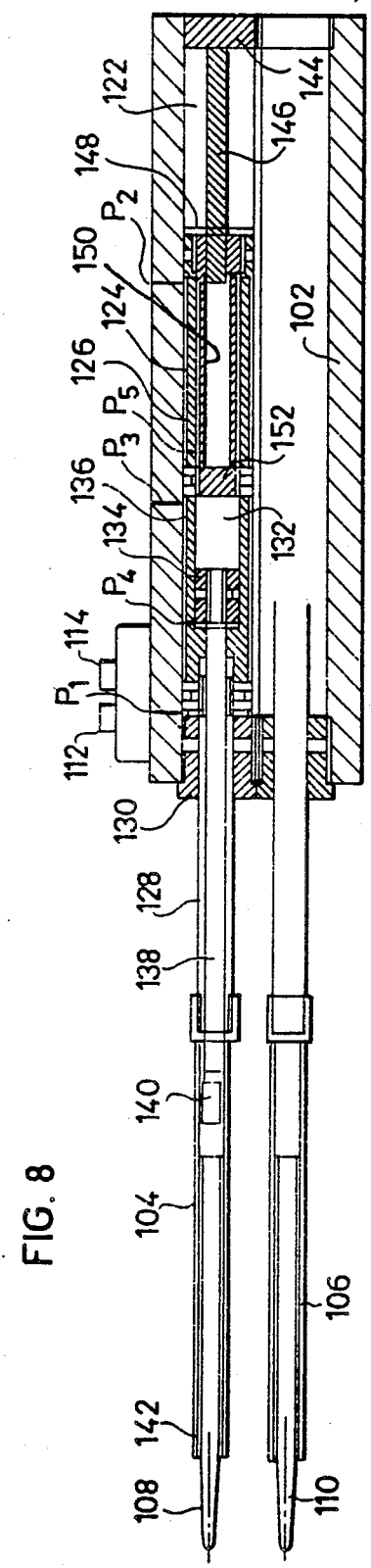
FIG. 8
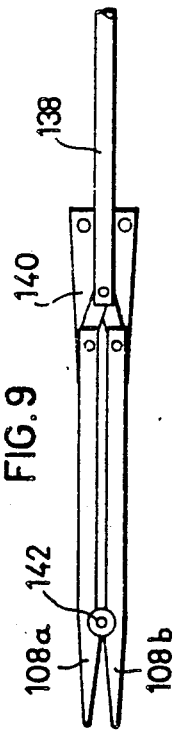
FIG. 9
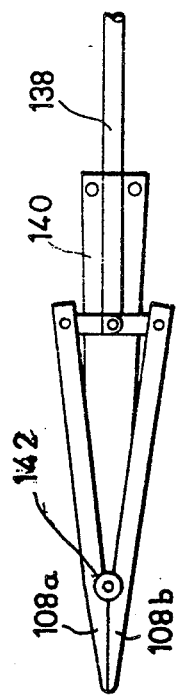
FIG 10
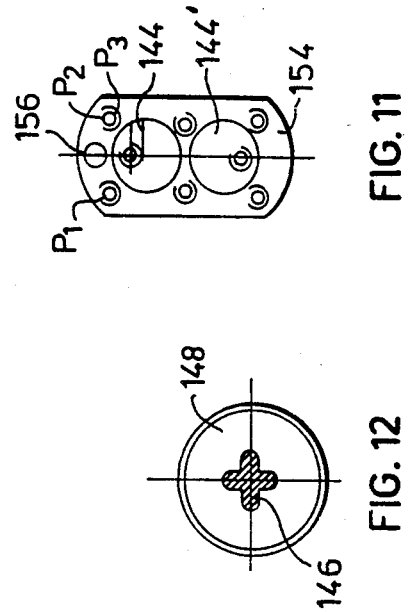
FIG. 11
FIG. 12

4,635,638

POWER-DRIVEN GRIPPING TOOL PARTICULARLY USEFUL AS A SUTURING DEVICE

BACKGROUND OF THE INVENTION

The present invention relates to power-driven gripping tools for gripping a member between a pair of jaws. The invention is particularly applicable to suturing devices for use by a surgeon in suturing a wound, and is therefore described below with respect to this application.

The suturing device of the present invention is particularly directed to assist the surgeon in suturing deep tissues especially in the abdominal region, for example, while performing Marshall Marchetti operations, gall bladder operations, intestinal operations, and the like. Suturing the tissues when performing such deep abdominal surgical operations is particularly difficult since the abdominal region is extremely crowded, obscuring the surgeon's vision and also requiring him frequently to move tissues aside in order to expose and view other tissues. In addition, the abdominal region contains abdominal fluids which further obscure the surgical area and also require draining. The present surgical techniques require the surgeon to use both his hands when inserting the suture needle containing the suture and pulling it out to perform the stitch. This not only deprives the surgeon from using one hand for exposing the surgical area or draining the abdominal fluids, but also tends to further obscure the surgical area; in addition, an assistant is frequently required to perform many of the tasks.

Several suturing devices have been previously proposed which include a handle having a pair of needle holders each movable to an extended position or to a retracted position, with each needle holder including a pair of gripper members movable to a closed position for gripping a needle therebetween, or to an open position releasing the needle. Examples of previously proposed suturing device of this type are described in U.S. Pat. Nos. 2,601,564 and 3,073,311. Insofar as we are aware, however, neither of these suturing devices has gained any widespread use, and this is probably because of the great manual effort required by the surgeon in moving the needle holders and also the pair of gripper members during the surgical operation.

One object of the present invention is to provide a new power-driven gripping tool particularly useful as a suturing device.

Another object of the present invention is to provide a suturing device having advantages over the previously known suturing devices of this type.

BRIEF SUMMARY OF THE INVENTION

According to one aspect of the present invention there is provided a suturing device comprising a handle grippable by the surgeon; a pair of needle holders extending parallel to each other from one end of the handle, and each movable to an extended, operative position, or to a retracted, inoperative position; each of the needle holders including a pair of gripper members movable to a closed position gripping a needle therebetween, or to an open position releasing the needle; characterized in that the handle further includes a power drive for driving the pair of needle holders to their extended and retracted positions, and for moving the pair of gripper members of each needle holder to their open and closed positions; and control means operable by the surgeon for selectively controlling the power drive.

A suturing device constructed in accordance with the foregoing features greatly assists the surgeon in suturing tissue, particularly in deep abdominal surgery. It enables him to perform the suturing with one hand, thereby leaving the other hand free for exposing particular surgical areas, draining fluids, and the like. Thus, the use of such a suturing device increases the efficiency at which the surgeon is able to perform the surgical operation, reduces the physical effort required by him in doing so, and frequently obviates the need of an assistant for performing many of the tasks required during such an operation, such as draining fluids, physically moving tissues, and the like, which the surgeon can now perform himself with his free hand.

According to another aspect of the present invention, there is provided a power-driven gripping tool comprises a housing having a first cylinder and a first piston movable within it to either a retracted or extended position. The first piston is formed with a bore defining a second cylinder, there being a second piston movable within the second cylinder to either a retracted or extended position. The first piston carries a first stem having a pair of gripper jaws pivotably mounted thereto; and the second piston carries a second stem having a coupling between the second stem and the gripper jaws for opening and closing the jaws by the movement of the second stem. The tool further includes control means for controlling the application of fluid pressure to the first and second cylinders to control the movement of the first and second pistons therein.

Further features and advantages of the invention will be apparent from the description below.

BRIEF DESCRIPTION OF THE DRAWINGS

The invention is herein described, by way of example only, with reference to the accompanying drawings, wherein:

FIG. 2 is a side elevational view, partly in section, of the suturing device illustrated in FIG. 1;

FIG. 3 is a top plan view of the device of FIG. 1;

FIG. 4 is a schematical end view of the device of FIG. 1;

FIG. 5 is a three-dimensional view illustrating one of the two sections forming the housing for the gripper jaws in one of the needle holders in the device of FIG. 1;

FIG. 6 is an end elevational view, partly broken away, illustrating one of the gripper jaws in the device of FIG. 1;

FIG. 7 illustrates the position of each of the two manual control buttons manipulated by the surgeon in the suturing device of FIG. 1;

FIG. 8 is a side elevational view, partly in section, of another form of suturing device constructed in accordance with the present invention;

FIG. 9 is a top plan view illustrating one of the pair of gripper jaws in the suturing device of FIG. 8, the jaws being shown in their open condition;

FIG. 10 is a view similar to that of FIG. 9 but showing the gripper jaws in their closed condition;

FIG. 11 is a rear view of the suturing device of FIG. 8; and

FIG. 12 is a sectional view of the rear guiding stem in FIG. 8.

DESCRIPTION OF PREFERRED EMBODIMENTS

The Embodiment of FIGS. 1-7

Figure 1:
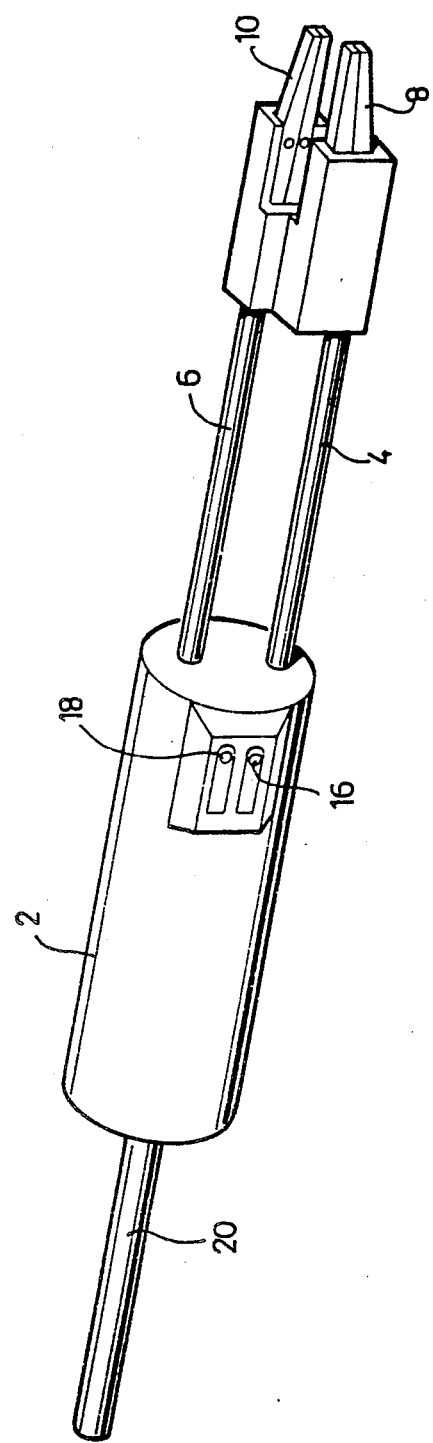
FIG. 1 is a three-dimensional view illustrating one form of suturing device constructed in accordance with the present invention.

FIGS. 1-7 illustrate a suturing device including a handle 2 grippable by the surgeon, and a pair of needle holders 4 and 6 extending parallel to each other from one end of the handle. Each needle holder is movable to an extended operative position, as shown in FIG. 1, or to a retracted inoperative position.

Each needle holder includes a pair of gripper members, indicated at 8 for holder 4 and at 10 for holder 6, which are movable to a closed positon for gripping a needle therebetween, or to an open position releasing the needle. FIG. 1 illustrates the gripper members 8 and 10 of both needle holders 4 and 6 in their closed positions for gripping the suturing needle (not shown).

FIG. 1 further illustrates two manually-movable buttons 16 and 18, respectively, manipulatable by the surgeon for controlling the needle holders 4 and 6 and their gripping members 8 and 10, as will be described more particularly below. Also illustrated in FIG. 1 is a tube 20 connecting the handle 2 to a supply of pressurized fluid, in this case pressurized air, for driving the needle holders and their gripper members under the control of the manual buttons 16 and 18, as will also be described more particularly below.

As shown particularly in FIG. 2, the drive for needle holder 4 comprises a cylinder 22 fixed within handle 2, and a piston 24 displaceable within the cylinder. Piston 24 carries a stem 26 to which is secured a second cylinder 28 having a second piston 30 displaceable therein. The latter piston carries a stem 32 extending through the housing end wall 34 and through the needle holder 4 into a second housing 36 fixed to the end of the needle holder. Piston stem 32 terminates in a conical tip 38 within housing 36.

Housing 36 houses the gripper members 8. These members are in the form of jaws pivotable on a pair of pins 8a extending in parallel to each other and transversely to the axis of piston stem 32. Each jaw is urged to its open position by a spring 40 received within notch 42 (FIG. 6) on the inner side of its hole 44 receiving pivot pin 8a. The two jaws are adapted to be moved to their closed positions by the conical tip 38 of piston stem 32, upon the extension of the piston stem. For this purpose, the lower inner edge of each jaw 8 is formed with a tapered surface, as shown at 44 in FIG. 6, which tapered surface receives conical tip 38 of stem 32 such that the extension of the piston stem cams the two jaws about their pivot pins 8a to close the outer ends of the jaws on the needle.

Housing 36, accomodating the pivotable jaws 8, is made in two sections, one of which is shown at 36a in FIG. 5. It will be seen that each section 36a is formed with a cavity 46 for accomodating the inner ends of the two pivotal jaws 8, and with two openings 48 for accomodating the two pivot pins 8a on which the jaws are pivotable. Each section further includes a bore 50 through its rear wall for accomodating the tip 38 of piston stem 32.

Cylinder 22, for driving needle holder 4 to its extended and retracted positions, is formed with a first port 52 on one side of piston 24 for introducing pressurized fluid in order to drive the piston to the extended position of needle holder 4, and with a second port 54 on the opposite side of piston 24 for driving the piston to the retracted position of the needle holder. Cylinder 28 carried at the end of piston stem 26 is formed with only one port 56 for driving its piston 30 to its extended position, the latter cylinder including a return spring 58 for returning the piston to its normal position.

It will be appreciated that the other needle holder 6 is similarly provided with a drive cylinder (corresponding to cylinder 22) for driving needle holder 6 to its extended and retracted positions, and with a second cylinder (corresponding to cylinder 28) for driving the two pivotable jaws 10 of the needle holder 6 to their open and closed positions.

Push buttons 16 and 18 carried by handle 2 control the application of the pressurized fluid to the above drive cylinders. Each of the two push buttons has three positions, as shown schematically in FIG. 7 with respect to push button 16. The full-line position of push button 16 in FIG. 7 is the home position, wherein its needle holder 4 is in its retracted position, and the two pivotable jaws 8 are pivoted open. Thus, in the full-line position of push button 16, the pressurized fluid would be supplied to port 54 of cylinder 22 to retract its needle holder 4, the jaws 8 being urged to their open positions by springs 40.

In order to drive needle holder 4 to its extended position, push button 16 is pushed to its position 16' in FIG. 7. When in this position, pressurized fluid is inletted into port 52 to drive piston 24 leftwardly in FIG. 2, the gripper jaws 8 still being biased to their open positions by springs 40. When it is desired to move the gripper jaws 8 to their closed positions to grip the needle 12, push button 16 is pushed to position 16" (FIG. 7). This inlets pressurized fluid via port 56 into cylinder 28, thereby driving piston 30 leftwardly such as to cause the conical tip 38 of piston stem 32 to engage tapered surfaces 44 of gripper jaws 8 to cam the gripper jaws to their closed positions gripping the suture needle 12. The surgeon may then manipulate the suturing device to insert the needle into tissue to be sutured, since the gripper jaws 8 of needle holder 4 firmly grip the needle.

When it is desired to pull out the needle to complete a stitch, push button 18 controlling needle holder 6 is moved by the surgeon first to drive needle holder 6 to its extended position, and then to close its gripping jaws 10 on the needle, in the same manner as described above with respect to push button 16. At this time, push button 16 may be moved from its position 16" (FIG. 7) to depressurize cylinder 28, whereupon spring 58 returns piston 30 to its retracted position, thereby causing jaws 8 to open under the influence of springs 40 to release the needle. The surgeon may then move push button 16 to its original positon, as shown in full lines in FIG. 7, causing holder 4 to be driven by piston 24 to its retracted inoperative position.

In this manner, the surgeon may manipulate the device while the sewing needle 12 is securely gripped by jaws 8 of needle holder 6, transferring the needle from one needle holder to the next. All these operations can be performed by one hand, thereby freeing the surgeons's other hand. This handling of the needle is facilitated by disposing the needle holders 4, 6 at one side of the center plane of handle 2 as shown in FIG. 4, such that their longitudinal axes are parallel to each other and to the longitudinal axis of the handle, but their transverse axes intersect each other at about 120° at the longitudinal axis of the handle.

The Embodiment of FIGS. 8–12

FIGS. 8–12 also illustrate a suturing device which includes a handle 102 grippable by the surgeon, and a pair of needle holders 104, 106 extending parallel to each other from one end of the handle. Each needle holder is movable to an extended operative position as shown in FIG. 8, or to a retracted inoperative position.

Each needle holder includes a pair of gripper jaws, 108, 110, which are movable to a closed position for gripping a needle therebetween, or to an open position releasing the needle, all under the control of slide buttons 112, 114. FIG. 9 illustrates gripper jaws 108 in their open position, and FIG. 10 illustrates them in their closed position. Handle 102 is supplied with pressurized fluid, for example pressurized air, by means of a tube (not shown) connected to the end of the handle opposite to the needle holders.

FIG. 8 illustrates the drive for one of the needle holders 104 and its pair of gripper jaws 108, it being appreciated that the drive for the other needle holder 106 and its gripper jaws 110 is of the same construction.

Thus, the drive illustrated in FIG. 8 for needle holder 104 and its gripper jaws 108 comprises a first cylinder 122 defined by a bore in housing 102, and a first piston 124 displacable within cylinder 122 to either a retracted position or an extended position; the latter is the position of cylinder 124 illustrated in FIG. 8. Piston 124 is moved to its retracted position by pressurized fluid applied to port $P_1$ in housing 102 at one end of cylinder 122, and piston 124 is moved to its extended (illustrated) position by pressurized fluid applied via port $P_2$; the latter port communicates with an annular recess 126 formed at the rear end of the piston.

A stem 128 is secured to the front end of piston 124 and extends through an opening in the front wall 130 of housing 102. Needle holder 104 is fixed to stem 128, so that the needle holder is moved to its extended and retracted positions with piston 124.

Piston 124 is formed with a bore 132 in which is movable a second piston 134. Thus, bore 132 within the first piston 124 serves as a cylinder for the second piston 134. The second piston 134 is moved to its retracted position by pressurized air applied via port $P_3$ through housing 102, annular recess 136 formed around the front part of piston 134, and a further port $P_4$ formed through the piston wall at its front end. Piston 134 is moved to its extended (illustrated) position by pressurized air applied via port $P_2$ through housing 102, and a further port $P_5$ through the wall of piston 134 at an intermediate location thereof. It will thus be seen that piston 134 is automatically actuated to its illustrated extended position whenever piston 124 is actuated to extend the needle holder 104.

Another stem 138 is coupled to piston 134 and extends through stem 128 to the front end of the needle holder 104, where it is coupled by linkage 140 to the two gripper jaws 108a, 108b. The latter jaws are pivotably mounted to the front, end of holder 104 by a pin 142. Linkage 140 is such that when stem 138 is moved to its extended position by the extension of its piston 134, the gripper jaws 108a, 108b are opened, as shown in FIG. 9; and when the stem is moved to its retracted position (FIG. 10), the gripper jaws are closed. Accordingly, since piston 134 is automatically extended with the extension of piston 124 within cyinder 122, it will be appreciated that the gripper jaws 108a, 108b are automatically opened with the extension of needle holder 104. In order to close the jaws, pressurized fluid must be applied via ports $P_3$ and $P_4$ to the front end of piston 134 to retract that piston and its stem 138.

The rear end of the bore within housing 102 serving as cylinder 122 is closed by a threadedly applied cap 144. A stem 146 is fixed to cap 144 to extend within cylinder 122 and passes through an opening in end wall 148 of piston 124.

As shown in FIG. 12, stem 146 is of non-circular cross-section, preferably of X-cross-section, and the opening through end wall 148 is of a complementary non-circular cross-section. Thus, wall 148, moving along stem 146 during the actuation and retraction of piston 124, constrains the movement of the piston to a linear movement, and prevents any rotation of the piston.

A tube 150 is secured at its rear end to wall 148 and extends within piston 124, the opposite end of tube 150 being closed by a front wall 152. Wall 152 serves as a stop engageable with the end of stem 146 to limit the retracted position of piston 124. This wall 152 also serves as a stop engageable with piston 134 to limit the retracted position of that piston.

As indicated earlier, housing 102 includes a second drive, exactly as described above, for the second needle holder 106 and its gripper jaws 110.

The rear end wall of housing 102 is shown in FIG. 11, therein designated 154, wherein it will be seen that it includes a cap 144 closing cylinder 122 of the drive for needle holder 104, and a similar cap 144' closing the corresponding cylinder for the drive of needle holder 106. End wall 154 further includes ports $P_1'$, $P_2$, and $P_3$, for introducing pressurized fluid into the housing as described above, there being three similar ports for the second drive within the housing. In addition, end wall 154 further includes an opening 156 for the electrical wires to the slide buttons 112, 114, one slide button controlling the drive for needle holder 104 and its gripper jaws 108, and the other button controlling the drive for needle holder 106 and its gripper jaws 110. Each of the two buttons preferably has three positions, namely: (1) a Home position, in which the respective needle holder is retracted, (2) an Extend position, wherein the needle holder is extended, the respective gripper jaws being automatically opened, and (3) a Grip position wherein the respective gripper jaws are closed while the respective needle holder is extended.

The suturing device illustrated in FIGS. 8–12 of the drawings may be operated as follows:

Whenever the surgeon wishes to grip the needle by one of the holders 104, 106, he moves the respective button 112 or 114 from its "Home" position to its "Extend" position. This causes pressurized fluid to be applied via port $P_2$ and recess 126 to move piston 124 to its extended position, as illustrated in FIG. 1. This actuation of piston 124 and its needle holder 104 to their extended positions also automatically moves piston 134 to its extended position, via the pressurized fluid applied to port $P_2$, recess 126 and port $P_5$ in the wall of piston 124. The movement of piston 134 to its extended position thus causes its clamping jaws to automatically open (FIG. 9).

Now, when the surgeon wishes to grip the needle by the clamping jaws, he actuates the respective button 116, 118 to move same to the "Grip" position. This causes pressurized fluid to be applied to port $P_4$, thereby moving piston 134 to its retracted position which, as illustrated in FIG. 10, closes the clamping jaws.

In this manner, the surgeon may manipulate the needle holders 104 and 106, and their clamping jaws 108 and 110, transferring the needle from one holder to the next as desired. All of this can be done with one hand under the control of buttons 112, 114, thereby freeing the surgeon's other hand for performing other tasks, e.g., exposing particular surgical areas or draining fluids.

While the invention has been described with respect to two preferred embodiments, it will be appreciated that many other variations, modifications and applications of the invention may be made.

What is claimed is:

1. A suturing device comprising a handle grippable by the surgeon; a pair of needle holders extending parallel to each other from one end of the handle, and each movable to an extended operative position or to a retracted, inoperative position; each of said needle holders including a pair of gripper members movable to a closed position gripping a needle therebetween, or to an open position releasing the needle; characterized in that said handle further includes a power drive for driving said pair of needle holders to their extended and retracted positions, and for moving said pair of gripper members of each needle holder to their open and closed positions; and control means operable by the surgeon for selectively controlling said power drive.

2. The device according to claim 1, wherein said power drive is disposed within said handle and includes a piston and cylinder for each of said pair of needle holders.

3. The device according to claim 2, wherein said power drive includes, for each of said pair of needle holders; a first piston and cylinder, one of which is displaceable with respect to the other, for driving the respective needle holder to its extended and retracted positions; and a second piston and cylinder carried by the displaceable one of said first piston and cylinder, for moving the pair of gripper members to their open and closed positions.

4. The device according to claim 1, wherein said pair of gripper members of each of said needle holders comprises a pair of jaws pivotably mounted at the end of an arm.

5. The device according to claim 4, wherein said pivotable jaws of each needle holder are spring-urged to their open positions and are pivoted to their closed positions by a piston movable within a cylinder disposed within said handle.

6. The device according to claim 5, wherein said jaws are pivotably mounted at an intermediate point to said arm, with the outer ends of the jaws engageable with the needle, said piston including a cam surface at its end engageable with the inner end of said jaws to pivot them to their closed positions upon the displacement of the piston within its cylinder.

7. The device according to claim 1, wherein said control means comprises a control button for each of said needle holders and slidable to a first position retracting the respective needle holder, to a second position extending the respective needle holder, or to a third position closing the gripper members.

8. The device according to claim 1, wherein said pair of needle holders have longitudinal axes parallel to each other and to the longitudinal axis of the handle, and transverse axes intersecting each other at about 120° at the longitudinal axis of the handle.

9. The device according to claim 1, wherein said power drive is a pneumatic drive operated by compressed air.

10. The device according to claim 1, wherein said power drive for driving each of said pair of needle holders comprises:
a first cylinder within said handle;
a first piston movable within said first cylinder to either a retracted or extended position therein;
a first stem carried by said first piston and movable therewith;
a second cylinder carried by said first stem;
a second piston movable within said second cylinder to either a retracted or extended position therein;
the respective pair of gripper jaws being pivotably carried by said first stem;
a second stem carried by said second piston and movable therewith to either a retracted or extended position;
and a coupling between said second stem and said pair of gripper jaws for opening and closing said jaws by the movement of said second stem;
said control means controlling the application of fluid pressure to said first and second cylinders to control the movement of said first and second pistons therein.

11. A power-driven gripping tool, comprising:
a housing having a first cylinder therein;
a first piston movable within said first cylinder to either a retracted or extended position therein;
a first stem carried by said first piston and movable therewith;
a second cylinder carried by said first stem;
a second piston movable within said second cylinder to either a retracted or extended position therein;
a pair of gripper jaws pivotably carried by said first stem;
a second stem carried by said second piston and movable therewith to either a retracted or extended position;
a coupling between said second stem and said gripper jaws for opening and closing said jaws by the movement of said second stem;
and control means for controlling the application of fluid pressure to said first and second cylinders to control the movement of said first and second pistons therein.

12. The tool according to claim 11, wherein said first cylinder and said first piston include cooperable guiding elements to constrain the movement of said first piston to linear movements.

13. The tool according to claim 12, wherein said cooperable guiding elements comprise a stem of non-circular cross-section fixed to an end wall of said first cylinder, and an end wall fixed to said first piston and formed with an opening of a complementary non-circular cross-section receiving said stem of the first cylinder and movable therealong during the movement of said first piston.

14. The tool according to claim 13, wherein said stem fixed to an end wall of said first cylinder, and said opening formed in an end wall fixed to said first piston, are both of X-cross-section.

15. The tool according to claim 13, wherein said first piston includes a tube secured at one end to said end wall thereof, and closed at its opposite end to engage the end of said stem fixed to the end wall of said first cylinder, and thereby to serve as a limit for the retracted position of said first piston.

16. The tool according to claim 15, wherein said closed end of said tube within said first piston is located so as to be engaged by said second piston, and thereby to serve as a limit for the retracted position of said second piston.

17. The tool according to claim 11, wherein said pair of gripper jaws are automatically opened when said first piston is moved to its extended position.

18. The tool according to claim 11, wherein said coupling between said second stem and said gripper jaws include links effective to open said jaws when said second stem is moved to its extended position, and to close said jaws when said second stem is moved to its retracted position.

19. The tool according to claim 11, wherein said control means comprises a control button for controlling the flow of fluid to said first and second cylinders for actuating said first and second pistons therein.

20. The tool according to claims 11, wherein the gripping tool is a suturing device including a pair of needle holders, a pair of gripper jaws for each of said needle holders, and a pair of said first and second cylinders and pistons for moving said needle holders and gripper jaws.

* * * * *

UNITED STATES PATENT AND TRADEMARK OFFICE
CERTIFICATE OF CORRECTION

PATENT NO. : 4,635,638
DATED : January 13, 1987
INVENTOR(S) : David Weintraub and Yaakov Zamir It is certified that error appears in the above-identified patent and that said Letters Patent are hereby corrected as shown below:

On Front Page, add to FOREIGN APPLICATION PRIORITY DATA

January 18, 1985 (IL)  Israel......74092

Signed and Sealed this

Second Day of August, 1988

Attest:

DONALD J. QUIGG

Attesting Officer

Commissioner of Patents and Trademarks